(12) United States Patent
Sugiura

(10) Patent No.: US 6,299,618 B1
(45) Date of Patent: Oct. 9, 2001

(54) INTRAOCULAR LENS INSERTION DEVICE

(76) Inventor: Takeshi Sugiura, Room No. 504, 29-16, Hirai 4-chome, Edogawa-ku, Tokyo (JP)

( * ) Notice: Subject to any disclaimer, the term of this patent is extended or adjusted under 35 U.S.C. 154(b) by 0 days.

(21) Appl. No.: 09/503,195

(22) Filed: Feb. 14, 2000

(30) Foreign Application Priority Data

Feb. 12, 1999 (JP) .................................................. 11-034168

(51) Int. Cl.[7] .................................................... A61F 9/00
(52) U.S. Cl. ........................................ 606/107; 623/6.12
(58) Field of Search ............................. 606/107; 623/6.12

(56) References Cited

U.S. PATENT DOCUMENTS

| | | | |
|---|---|---|---|
| 4,349,027 | * 9/1982 | DiFrancesco | 623/6.12 |
| 5,718,677 | * 2/1998 | Capetan et al. | 606/107 |
| 5,908,404 | * 6/1999 | Elliott | 606/107 |
| 6,059,292 | * 5/2000 | Josephberg | 606/107 |
| 6,156,042 | * 12/2000 | Aramant | 606/107 |
| 6,159,218 | * 12/2000 | Aramant et al. | 606/107 |
| 6,162,229 | * 12/2000 | Feingold et al. | 623/6.12 |

* cited by examiner

Primary Examiner—Paul J. Hirsch
(74) Attorney, Agent, or Firm—Browdy and Neimark

(57) ABSTRACT

An intraocular lens insertion device comprises a pad formed by an elastic element harmless to a living body, a drawing thread mounted on a rear portion of the pad, and an insert portion formed at a front portion of the pad. The insert portion has a shape suitable to fit into a ciliary sulcus of an aphakic eye. The pad has a thickness capable of covering a tip end of a surgical needle.

7 Claims, 6 Drawing Sheets

INTRAOCULAR LENS INSERTION DEVICE

FIELD OF THE INVENTION

The present invention relates to an intraocular lens insertion device, and, more particularly, to an insertion device which is employed when a posterior chamber lens is sutured on an aphakic eye from which a posterior capsule of lens has been extracted or lost due to cataract surgery, accident or injury.

PRIOR ART

Conventionally, a lens whitened by a cataract is extracted by surgical means. As shown in FIG. 1 and FIG. 2, a lens 10 has a nucleus 11 and a cortex 12, and the entire is capsulated by a lens capsule 13. At a time when an intraocular lens was not developed, the nebular or whitened lens 10 was extracted by ICCE (Intracapsular Cataract Extraction) together with the entire lens capsule 13 or was extracted by ECCE (Entracapsular Cataract Extraction) while a posterior capsule 14 of the lens capsule 13 was left. In cataract surgery at this period, the intraocular lens could not be used, and the patient required very thick eyeglasses for correcting an intense hypermetropia.

Thereafter, as an intraocular lens, an anterior chamber lens to be inserted into an anterior chamber 15 of the eye was developed. The anterior chamber lens could be inserted into an aphakic eye to which ICCE or ECCE had been applied. However, the anterior chamber lens caused complications such as bullous keratopathy at a high rate, and thus, the anterior chamber lens was obsolete.

In place of the anterior chamber lens, a posterior chamber lens 16 to be inserted into the lens capsule 13 was developed. The posterior chamber lens 16 brought a relatively good eyesight to the patient without causing postoperative complications. In a current, typical cataract surgery employing the posterior chamber lens 16, an anterior capsule 17 of the lens capsule 13 is cutout in a circular shape, the nucleus 11 and the cortex 12 inside the lens capsule 13 are removed by employing a phacoemulsifier aspirator, and then, the posterior chamber lens 16 is inserted into the lens capsule 13. As shown in FIG. 3, the posterior chamber lens 16 has a pair of elongated elastic supporters (haptics) 18, 18. The haptics 18, 18 are expanded within the lens capsule 13 by their own resilience, and abut against an inner surface 19 of the lens capsule 13, thereby maintaining the posterior chamber lens 16 at its predetermined position.

The posterior lens 16 had a further advantage that the lens can be mounted to an eye to which a traditional cataract surgery had been applied. In the case of the patient undergoing ECCE for extracting the lens 10 leaving the posterior capsule 14 of the lens capsule, an easy, simple operation, i.e., inserting the posterior lens 16 into the left lens capsule 13 became possible.

The posterior lens 16 could be also mounted on an eye from which the entire lens 10 had been extracted by ICCE. In order to mount the posterior lens 16 on an eye which has no lens 10, i.e., no tissues for supporting the posterior lens 16, "ab externo approach" and "ab interno approach" were developed. In any approach, the haptics 18 of the posterior lens 16 is inserted into a ciliary sulcus 22 between an iris 20 and a ciliary body 21, and is sutured on a sclera 23 with a thread. In these two approaches, a direction in which a needle is passed through the sclera 23 is different from another one.

FIG. 4A to FIG. 4E show a process of the ab externo approach. In the ab externo approach, a piercing needle 26 through which a thread 25 with a suturing needle 24 is inserted is passed through an eye from the outside of the eye to the inside of the eye via the ciliary sulcus 22 (FIG. 4A), a hook 28 is inserted into the inside of the eye via an incision 27 formed at the sclera 23, and a part of the thread 25 in the eye is pulled out by the hook 28 to the outside of the eye (FIG. 4B). Then, when a free end 29 of the thread 25 is completely pulled out via the incision 27 to the outside of the eye, and the suture needle 26 is removed from the eye, the state shown in FIG. 4C is obtained. In this state, the free end 29 of the thread 25 is tied with the first haptics 18 of the posterior chamber lens 16, and a free end 29 of another thread 25 treated similarly is tied with the second haptics 18 (FIG. 4D). Next, when the posterior chamber lens 16 is inserted into the inside of the eye via the incision 27, and the threads 25, 25 are pulled, the haptics 18, 18 are introduced to the ciliary sulcus 22, and finally, the threads 25 are sutured on the sclera 23 by the needle 24. In this manner, as shown in FIG. 4E, insertion of the posterior chamber lens 16 is completed.

FIGS. 5A to 5E show a process of the ab interno approach. In the ab interno approach, a weak curved suturing needle 24 with the thread 25 is inserted into the inside of the eye via the incision 27 of the sclera 23 (FIG. 5A), the needle 24 is put into the ciliary sulcus 22 (FIG. 5B), and then the needle 24 is pulled out to the outside of the eye (FIG. 5C). Next, the free end 29 of the thread 25 is tied with the first haptics 18 of the posterior chamber lens 16, and another thread 25 treated similarly is tied with the second haptics 18 (FIG. 5D). And, when the posterior chamber lens 16 is inserted into the inside of the eye via the incision 27, and the threads 25, 25 are pulled, the haptics 18, 18 are guided to the ciliary sulcus 22, and finally, the threads 25 are sutured on the sclera 23 by the needle 24. In this manner, as shown in FIG. 5E, insertion of the posterior chamber lens 16 is completed.

The most disadvantageous point in the ab externo approach and the ab interno approach is that it is difficult to accurately guide the needle 24 or 26 to the ciliary sulcus 22. In the ab externo approach, although the needle 26 is put into the sclera 23 based on the instinct and experience of the surgeon, there is no guarantee that the needle 26 is accurately guided to the ciliary sulcus 22. In the ab interno approach, since the ciliary sulcus 22 is hidden by the iris 20, the needle 24 advances toward the ciliary sulcus 22 blindly. Inaccurate needle insertion damages the ciliary sulcus 22 or iris 20. In addition, if the haptics 18 are not correctly fitted to the ciliary sulcus 22, a good eyesight cannot be expected.

SUMMARY OF THE INVENTION

An object of the present invention is to provide an intraocular lens insertion device to be used when the needle is put into the ciliary sulcus by the ab interno approach. This insertion device guides the needle to the ciliary sulcus accurately, can fit the haptics to the ciliary sulcus correctly, and prevents undesirable invasion.

PREFERRED EMBODIMENT OF THE INVENTION

Figure 6:
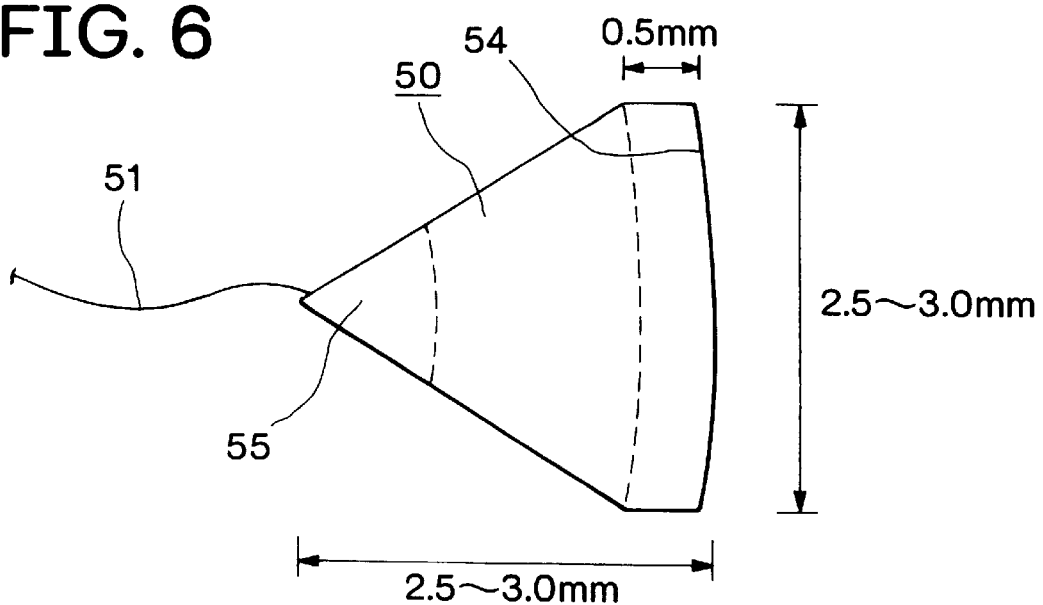
FIG. 6 is a plan view of an insertion device according to the present invention.
Figure 7:
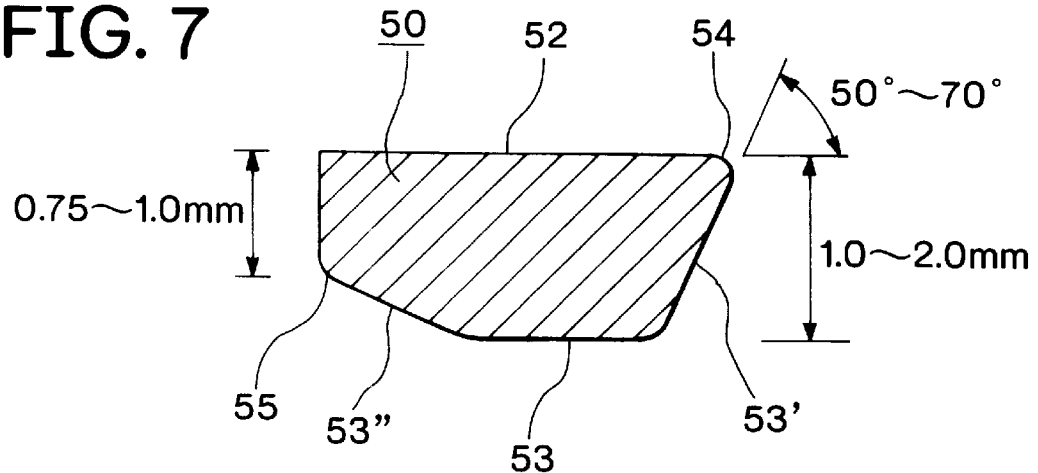
FIG. 7 is a sectional view of the insertion device.
Figure 8:
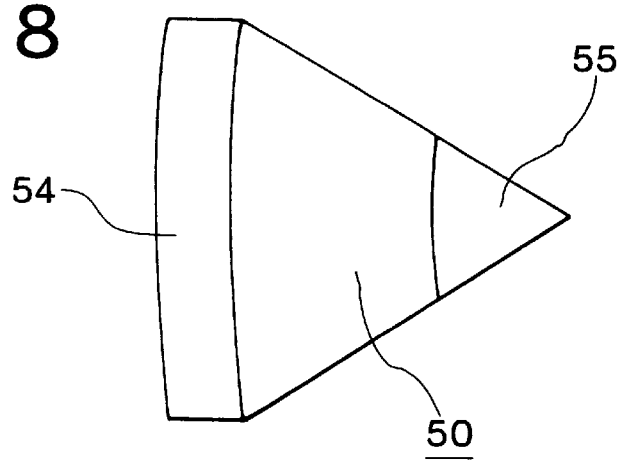
FIG. 8 is a bottom face view of the insertion device.

The preferred embodiment of the present invention will be described with reference to the accompanying drawings. As shown in FIG. 6 to FIG. 8, an intraocular lens insertion device according to the present invention comprises a pad 50 formed by an elastic element harmless to a living body such as silicon rubber or silicon sponge, and a drawing thread 51 mounted at a rear portion of the pad 50. The insertion device is used when the posterior chamber lens 16 is mounted on an eye which has no lens capsule 13, i.e., no site for supporting the posterior lens 16.

Figure 9A:
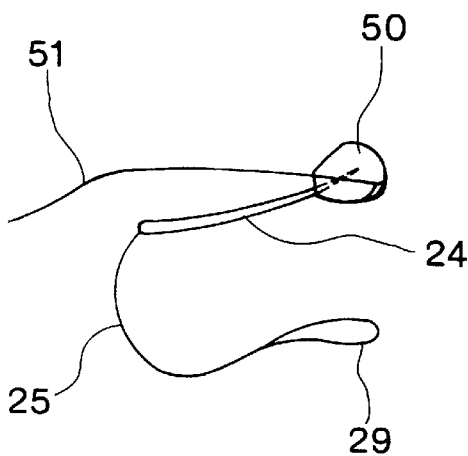
FIG. 9A to FIG. 9G are schematic views showing procedures for using the insertion device.
Figure 9B:
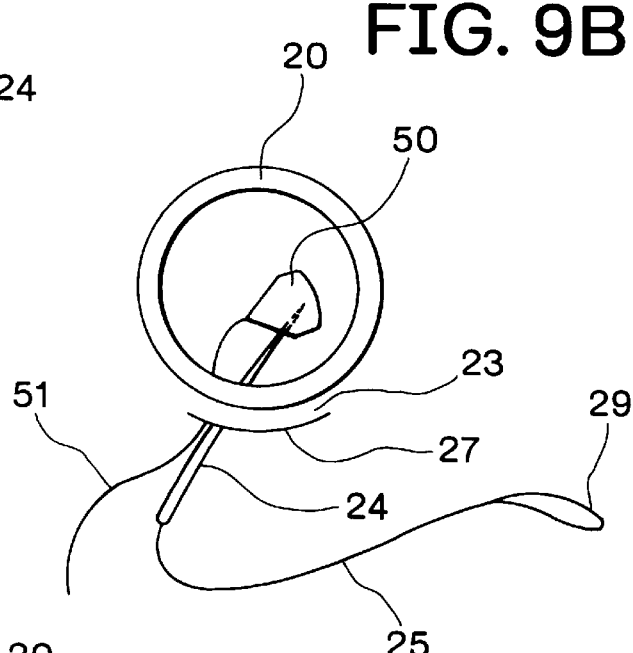

The pad 50 is substantially arc-shaped in a plan view, and an upper face 52 of the pad 50 is substantially flat as shown in FIG. 7. An inclined surface 53' on the front side of a lower surface 53 of the pad 50 is inclined toward the upper surface 52, where a taper-shaped insert portion 54 is formed. The pad 50 has a thickness of 1.0 to 2.0 mm at the thickest center thereof. While in use, as shown in FIG. 9A, a tip end of the straight needle or weak curved needle 24 equipped with the loop-shaped thread 25 is put into the pad 50 from the posterior part toward the anterior part. At this time, the tip end of the needle 24 must not be pierced from the pad 50.

Figure 9C:
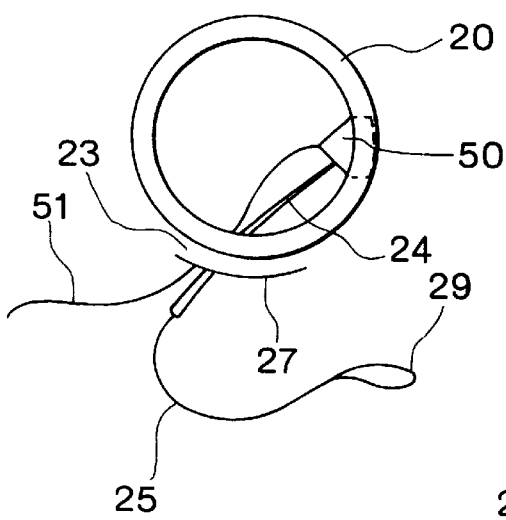
Figure 9D:
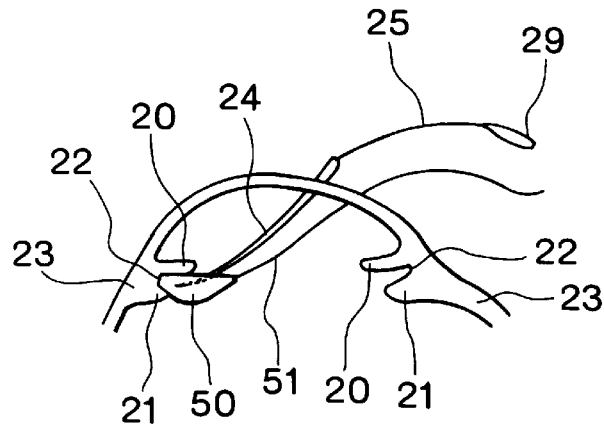

The pad 50 into which the tip end of the needle 24 is put is inserted into an aphakic eye via the incision 27 formed at the sclera 23, and then, the insert portion 54 of the pad 50 is slid at the back side of the iris 20 toward the ciliary sulcus 22. When the insert portion 54 is slid to the outside at the back side of the iris 20, it is easily and accurately guided to the ciliary sulcus 22 (FIG. 9C and FIG. 9D). At this time, the tip end of the needle 24 is covered with the pad 50, and thus, the eye is never damaged by the needle 24.

The insert portion 54 has a length of 2.5 to 3.0 mm and a width of about 0.5 mm. The tip end side of the insert portion 54 is formed in an arc shape having its radius of curvature of 10 to 12 mm. An angle between the upper surface 52 and the inclined surface 53 is between 50 and 70 degrees. The insert portion 54 having such shape is securely fitted to the ciliary sulcus 22, as shown in FIG. 9D, after the sliding movement of the insert portion 54 toward the ciliary sulcus 22. Accurate fitting of the insert portion 54 into the ciliary sulcus 22 is confirmed, if the pad 50 is immovable when the gentle force in a vertical direction is applied to the pad 50. The shape of the insert portion 54 defined as described above is determined with the basis of data which are found out by measuring a number of samples of the ciliary sulcus in the aphakic eyes with no posterior capsule with an ultrasound biomicroscopy (UBM).

Figure 9E:
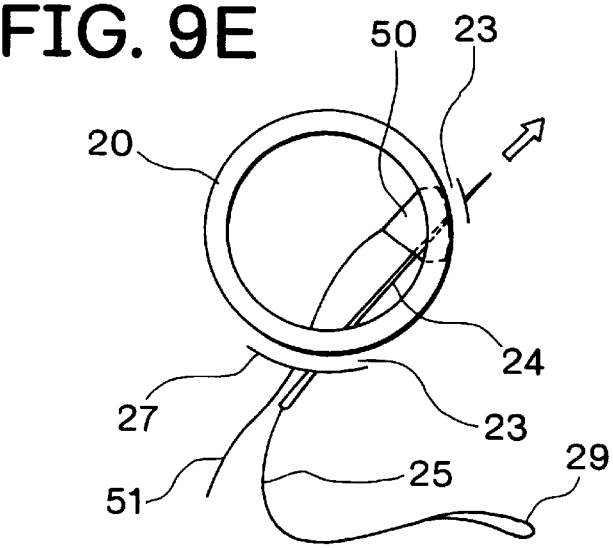
Figure 9F:
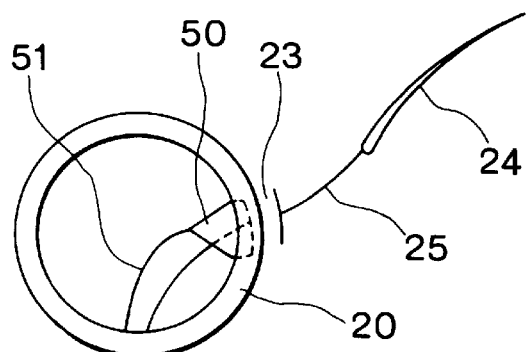
Figure 9G:
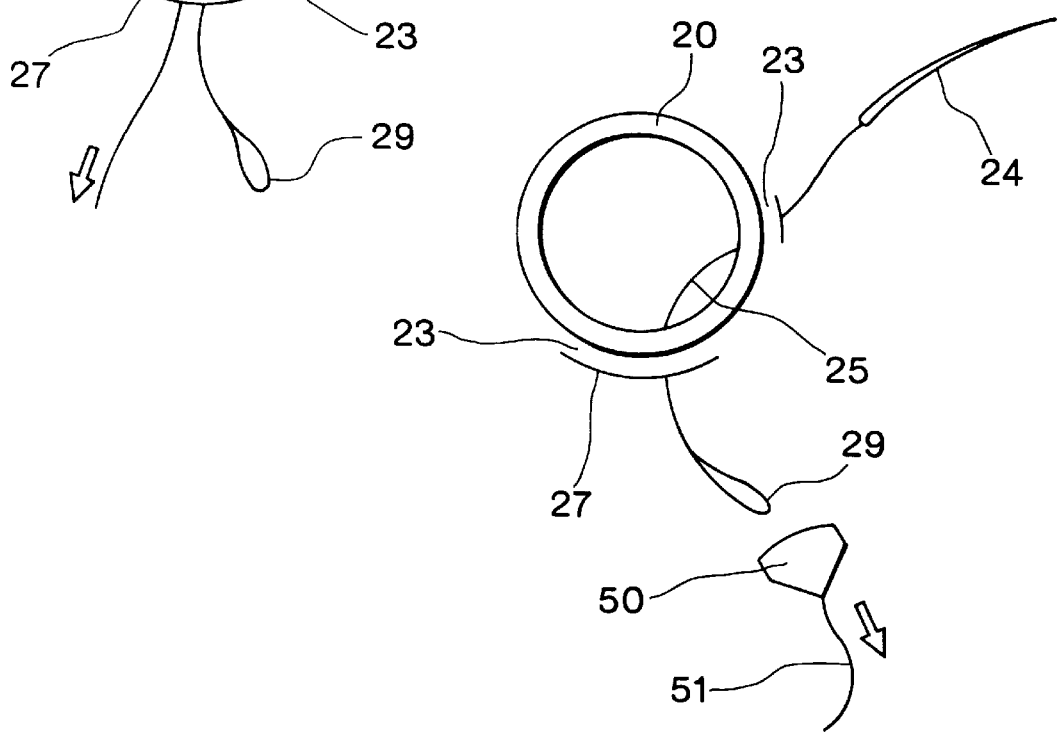

In the state shown in FIG. 9C and FIG. 9D, when the needle 24 is further pushed toward the sclera 23, the tip end of the needle 24 is pierced from the pad 50, and is guided to the ciliary sulcus 22 accurately and reliably. Thereafter, as shown in FIG. 9E, the needle 24 is protruded to the outside of the eye over the sclera 23. Next, after the needle 24 has been completely pulled out to the outside of the eye (FIG. 9F), when the drawing thread 51 of the pad 50 is pulled out, the pad 50 is taken out to the outside of the eye via the incision 27, and the state shown in FIG. 9G is obtained. An inclined surface 53" is provided at the rear side of the lower surface 53 of the pad 50 to define a taper-shaped drawing portion 55. The drawing portion 55 facilitates taking out the pad 50 to the outside of the eye via the incision 27.

In this manner, the first thread 25 for fixing the haptics 18 of the posterior chamber lens 16 to the ciliary sulcus 22 is accurately passed from the inside of the eye to the outside of the eye via the ciliary sulcus 22.

Figure 1:
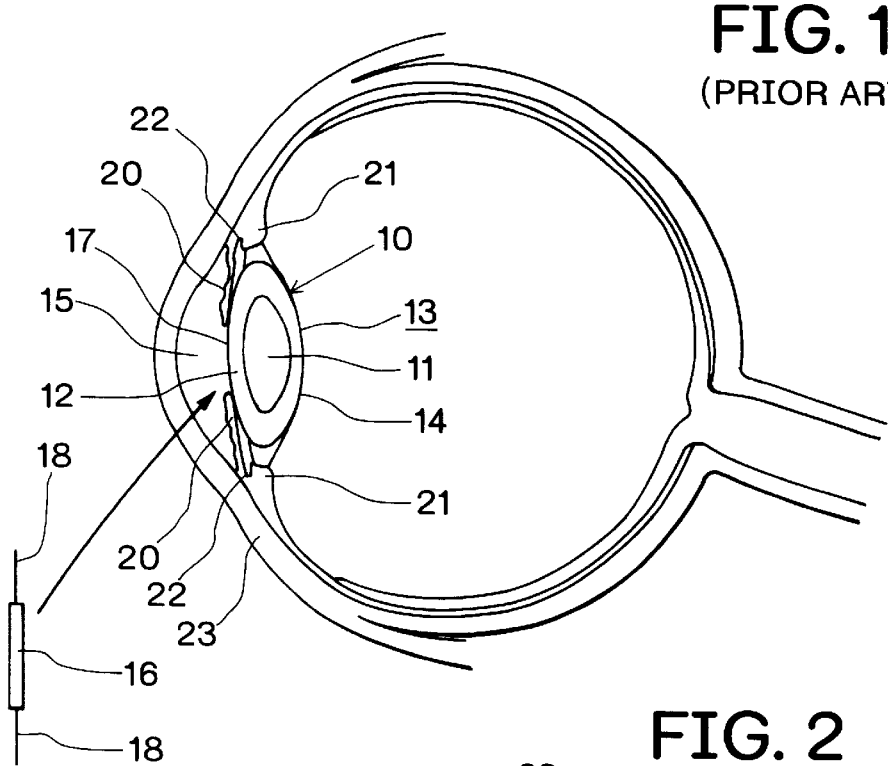
FIG. 1 is a sectional view showing a human eyeball.
Figure 2:
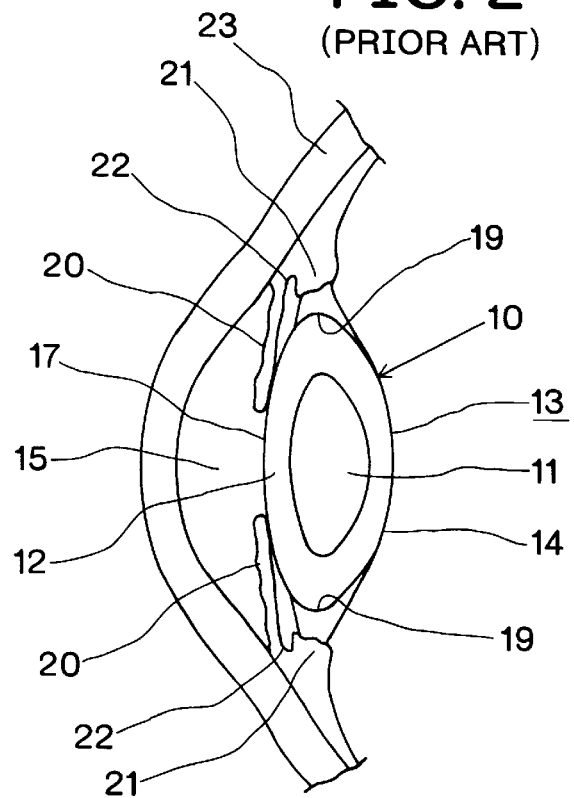
FIG. 2 is an enlarged sectional view showing a frontal part of the eyeball.
Figure 3:
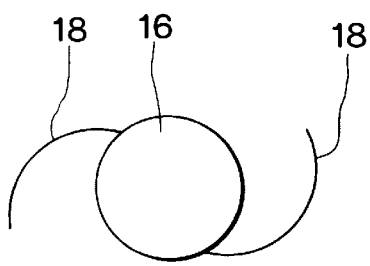
FIG. 3 is a plan view showing a posterior chamber lens.
Figure 4A:
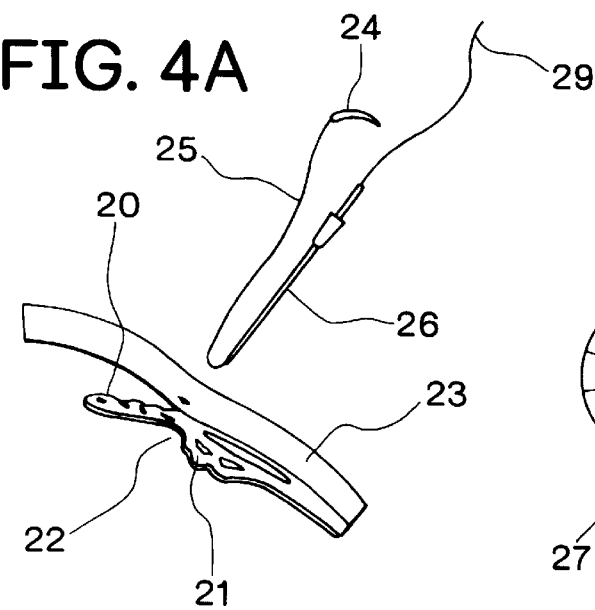
FIG. 4A to FIG. 4E are schematic views showing a process of an ab externo approach.
Figure 4B:
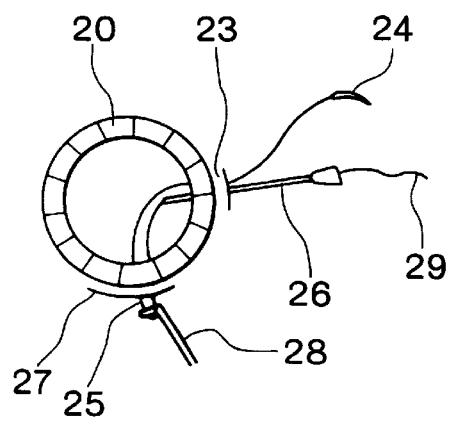
Figure 4C:
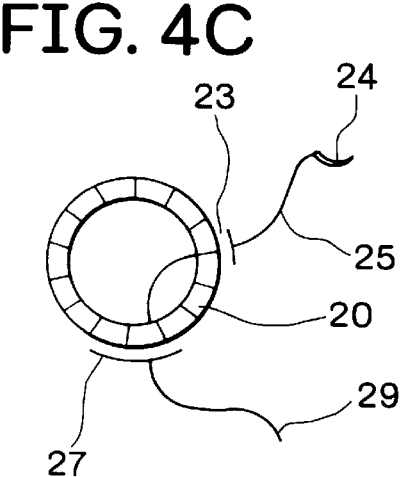
Figure 4D:
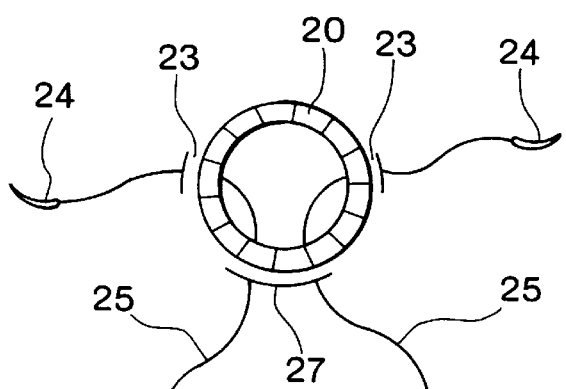
Figure 4E:
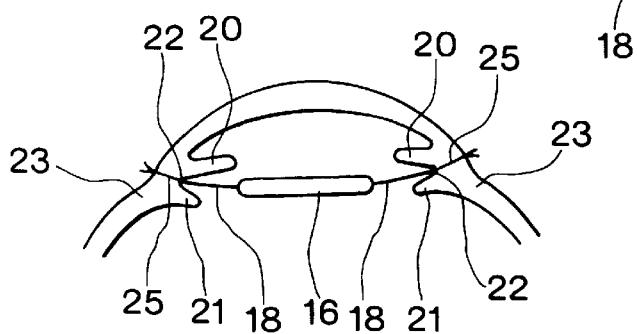
Figure 5A:
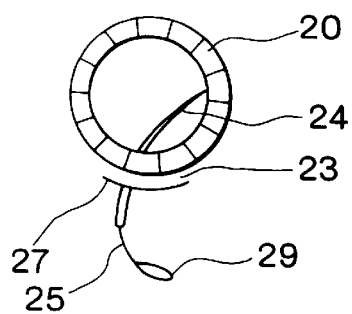
FIG. 5A to FIG. 5E are schematic views showing a process of an ab interno approach.
Figure 5B:
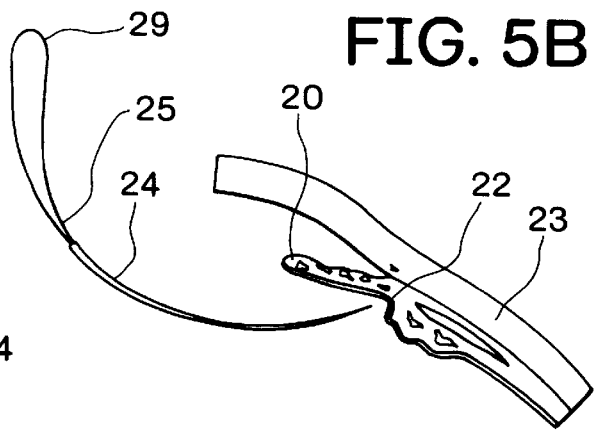
Figure 5C:
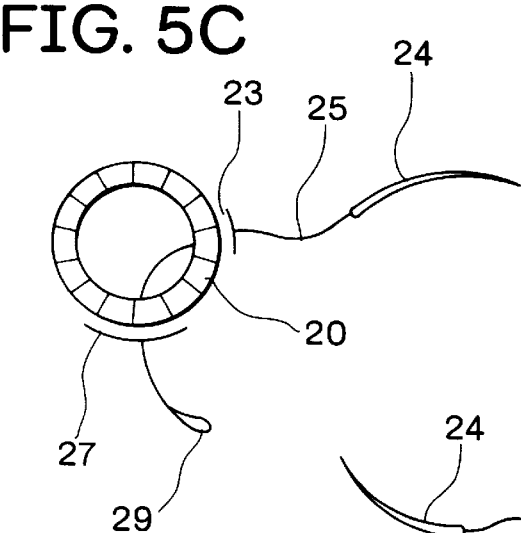
Figure 5D:
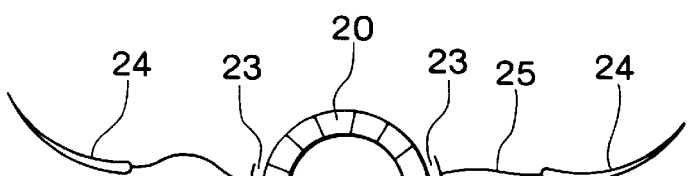
Figure 5E:
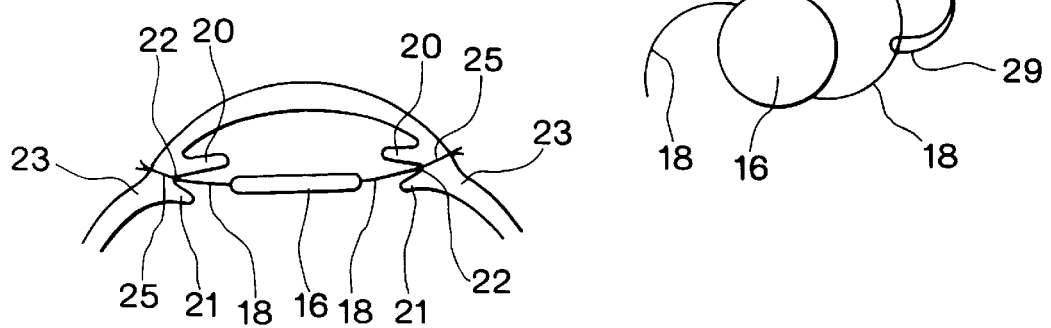

When the second thread 25 is passed through the ciliary sulcus 22 on the opposite side of the eye similarly, the state identical to one of the procedures for the conventional ab interno approach shown in FIG. 5D is obtained. Thereafter, the free ends 29, 29 of the threads 25, 25 are tied with haptics 18, 18 of the posterior chamber lens 16, and the posterior chamber lens 16 can be mounted in the procedure identical to the conventional procedure.

ADVANTAGE OF THE INVENTION

As is obvious from the foregoing description, when the pad 50 according to the present invention is employed, the needle 24 is guided to the ciliary sulcus 22 accurately and easily. Thus, the posterior chamber lens 16 can be accurately mounted on the aphakic eye from which the entire lens 10 has been extracted and lost. Further, since the tip end of the needle 24 is covered with the pad 50 at the inside of the eye, the needle 24 is effectively prevented from damaging the eye.

What is claimed is:

1. An intraocular lens insertion device comprising:

a pad formed by an elastic element harmless to a living body;

a drawing thread mounted on a rear portion of the pad; and an insert portion formed at a front portion of the pad and having a shape suitable to fit into a ciliary sulcus of an aphakic eye;

wherein said pad has a thickness capable of covering a tip end of a surgical needle.

2. The intraocular lens insertion device according to claim 1, wherein said insert portion is formed into a taper shape which becomes thinner in a forward direction thereof in a side view.

3. The intraocular lens insertion device according to claim 2, wherein an angle between an upper surface and a lower surface of said insert portion is between 50 and 70 degrees.

4. The intraocular lens insertion device according to claim 1, wherein said insert portion has an arc-shaped peripheral rim in a planar view.

5. The intraocular lens insertion device according to claim 4, wherein said peripheral rim has a length of 2.5 to 3.0 mm in the planar view.

6. The intraocular lens insertion device according to claim 5, wherein said peripheral rim has a radius of 10 to 12 mm.

7. The intraocular lens insertion device according to claim 1, wherein a taper-shaped drawing portion becoming thinner in a backward direction is formed at said rear portion of said pad.

* * * * *